(12) United States Patent
Kovi et al.

(10) Patent No.: US 10,221,184 B2
(45) Date of Patent: Mar. 5, 2019

(54) POLYMORPHS OF PONATINIB HYDROCHLORIDE

(71) Applicant: Apicore US LLC, Somerset, NJ (US)

(72) Inventors: Ravishanker Kovi, Monroe, NJ (US); Jayaraman Kannapan, Vadodara (IN); Ananda Babu Thirunavakarasu, Vadodara (IN); Gaurav Yadav, Utter Pradesh (IN); Veerabhadra Rao Bobbili, Andhra Pradesh (IN); Shivnath Sahebrao Patil, Maharashtra (IN); Sanjay F. Thakor, Vadodara (IN)

(73) Assignee: Apicore US LLC, Canonsburg, PA (US)

( * ) Notice: Subject to any disclaimer, the term of this patent is extended or adjusted under 35 U.S.C. 154(b) by 0 days.

(21) Appl. No.: 15/862,355

(22) Filed: Jan. 4, 2018

(65) Prior Publication Data

US 2018/0208599 A1   Jul. 26, 2018

Related U.S. Application Data

(60) Provisional application No. 62/448,787, filed on Jan. 20, 2017.

(51) Int. Cl.
  *C07D 487/04* (2006.01)
  *A61K 31/5025* (2006.01)
  *B01D 9/00* (2006.01)

(52) U.S. Cl.
  CPC .......... *C07D 487/04* (2013.01); *B01D 9/005* (2013.01); *B01D 9/0036* (2013.01); *C07B 2200/13* (2013.01)

(58) Field of Classification Search
  CPC .................................................. C07D 487/04
  See application file for complete search history.

(56) References Cited

U.S. PATENT DOCUMENTS

| 8,114,874 | B2 | 2/2012 | Zou |
| 9,493,470 | B2 | 11/2016 | Murray |
| 2016/0297821 | A1 | 10/2016 | Stefinovic |

*Primary Examiner* — Emily A Bernhardt

(57) ABSTRACT

Novel crystalline ponatinib hydrochloride forms designated Form alpha and Form beta are disclosed. Form alpha is characterized by data selected from an XRPD pattern with peaks at about 6.5, 9.0, 12.25, 14.4, 16.70, 19.6, 22.2, 24.5, 28.2±0.2 degrees 2-theta; an XRPD pattern substantially as depicted in FIG. 1; and/or a combination thereof. Form beta is characterized by data selected from an XRPD pattern with peaks at about 10.7, 15.2, 15.8, 16.4 23.1, 25.0, 27.8±0.2 degrees 2-theta; an XRPD pattern substantially as depicted in FIG. 3; and/or combinations thereof. Processes for making Form alpha and Form beta are disclosed.

12 Claims, 7 Drawing Sheets

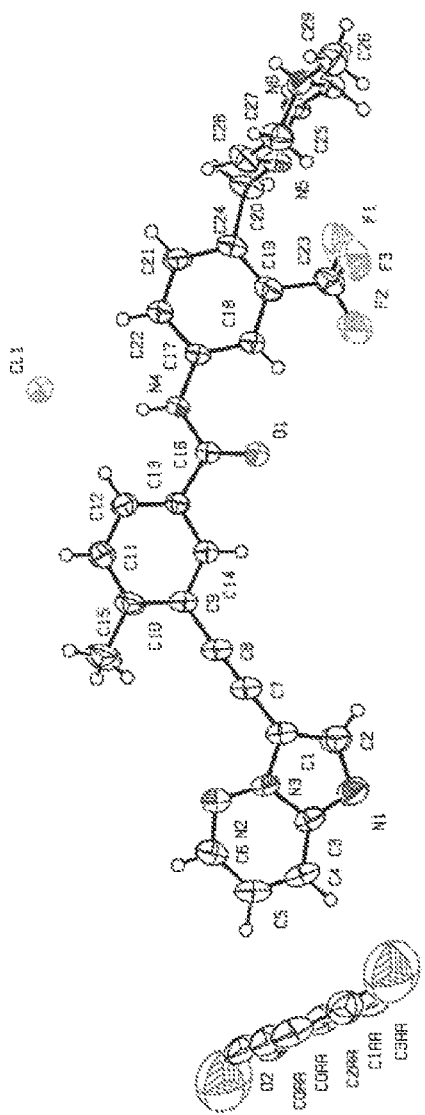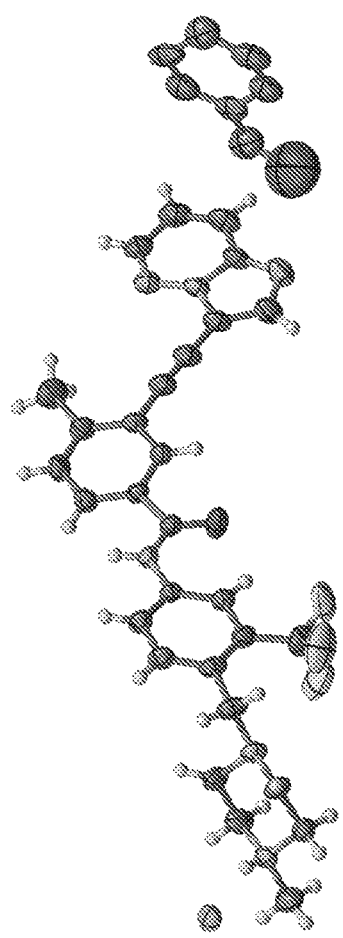
FIG. 6
FIG. 6A

POLYMORPHS OF PONATINIB HYDROCHLORIDE

CROSS-REFERENCE TO RELATED APPLICATIONS

This non-provisional application claims the benefit of U.S. Provisional Patent Application No. 62/448,787 filed Jan. 20, 2017, the entirety of which is incorporated herein by reference.

FIELD OF THE INVENTION

The present invention relates to ponatinib hydrochloride of formula I. Specifically, the present invention relates to novel crystalline forms of ponatinib hydrochloride and processes for the preparation of such novel polymorphs.

BACKGROUND OF THE INVENTION

Ponatinib is a kinase inhibitor. The chemical name for ponatinib hydrochloride is 3-(imidazo[1,2-b]pyridazin-3yl-ethynyl)-4-methyl-N-{4-[(4-methylpiperazin-1-yl)methyl]-3-(trifluoromethyl)phenyl}benzamide hydrochloride. The molecular formula is $C_{29}H_{28}ClF_3N_6O$ which corresponds to a formula weight of 569.02 g/mol. Its structure is shown below:

Formula I

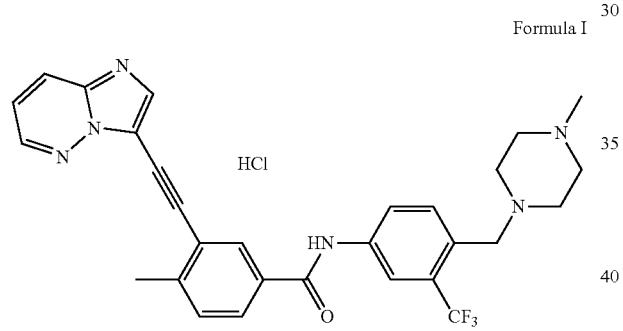

Ponatinib hydrochloride is marketed by Ariad Pharmaceuticals, Inc. under the trade name Iclusig®. Iclusig® tablets are available as white, round, film-coated tablets for oral administration. Each tablet contains ponatinib hydrochloride equivalent to 15, 30 or 45 mg ponatinib with the following inactive ingredients: lactose monohydrate, microcrystalline cellulose, sodium starch glycolate (type B), colloidal silicon dioxide, magnesium stearate and a tablet coating. The tablet coating consists of talc, polyethylene glycol, polyvinyl alcohol, and titanium dioxide. Ponatinib is disclosed in U.S. Pat. No. 8,114,874.

SUMMARY OF THE INVENTION

The discovery of new polymorphic forms and/or solvates of a drug or a pharmaceutically useful compound provides the opportunity to improve the characteristics of a pharmaceutically acceptable dosage form of the drug with a targeted release profile or other desired characteristics. U.S. Pat. No. 9,493,470 discloses various crystalline polymorphic forms of ponatinib hydrochloride such as forms A, B, C, D, E, F, G and H. U.S. Published Patent Application 20160297821 appears to disclose crystalline polymorphic forms of ponatinib hydrochloride characterized by XRPD. Yet there remains a need for new polymorphic forms of ponatinib hydrochloride and processes for their preparation.

Disclosed herein are crystalline forms of ponatinib hydrochloride designated as Form alpha, Form beta, and processes for the preparation thereof.

In an embodiment, the present disclosure provides crystalline ponatinib hydrochloride, namely ponatinib hydrochloride propylene glycol solvate, designated as Form alpha, characterized by data selected from an x-ray powder diffraction (XRPD) pattern with peaks at about 6.5, 9.0, 12.25, 14.4, 16.70, 19.6, 22.2, 24.5, 28.2±0.2 degrees 2-theta; an XRPD pattern substantially as depicted in FIG. 1; and/or combinations thereof.

In another embodiment, the present disclosure provides a process for preparing ponatinib hydrochloride Form alpha including the steps of:
  a. obtaining a solution of propylene glycol and ponatinib hydrochloride;
  b. maintaining the solution of step a) at a temperature of about 0° C. to about 150° C.; and
  c. isolating ponatinib hydrochloride propylene glycol solvate designated Form alpha from the solution.

In an embodiment, the present disclosure provides crystalline ponatinib hydrochloride, namely ponatinib hydrochloride benzyl alcohol solvate, designated as Form beta, characterized by data selected from an XRPD pattern with peaks at about 10.7, 15.2, 15.8, 16.4 23.1, 25.0, 27.8±0.2 degrees 2-theta; an XRPD pattern substantially as depicted in FIG. 4; and/or combinations thereof.

In another embodiment, the present disclosure encompasses a process for preparing ponatinib hydrochloride Form beta including the steps of:
  a. obtaining a solution of benzyl alcohol and ponatinib hydrochloride;
  b. maintaining the solution of step a) at a temperature of about 50° C. to about 150° C.; and
  c. isolating ponatinib hydrochloride benzyl alcohol solvate designated Form beta from the solution.

BRIEF DESCRIPTION OF THE DRAWINGS

For the purposes of illustration, there are forms shown in the drawings that are presently preferred, it being understood, however, that the invention is not limited to the precise arrangements and instrumentalities shown.

FIGS. 6 and 6A are diagrammatic representations of an X-ray crystal structure of ponatinib HCl Form beta according to an embodiment of the present disclosure.

DETAILED DESCRIPTION OF THE PREFERRED EMBODIMENTS

The present disclosure provides crystalline forms of ponatinib hydrochloride designated as Form alpha, Form beta and processes for the preparation thereof.

Figure 1:
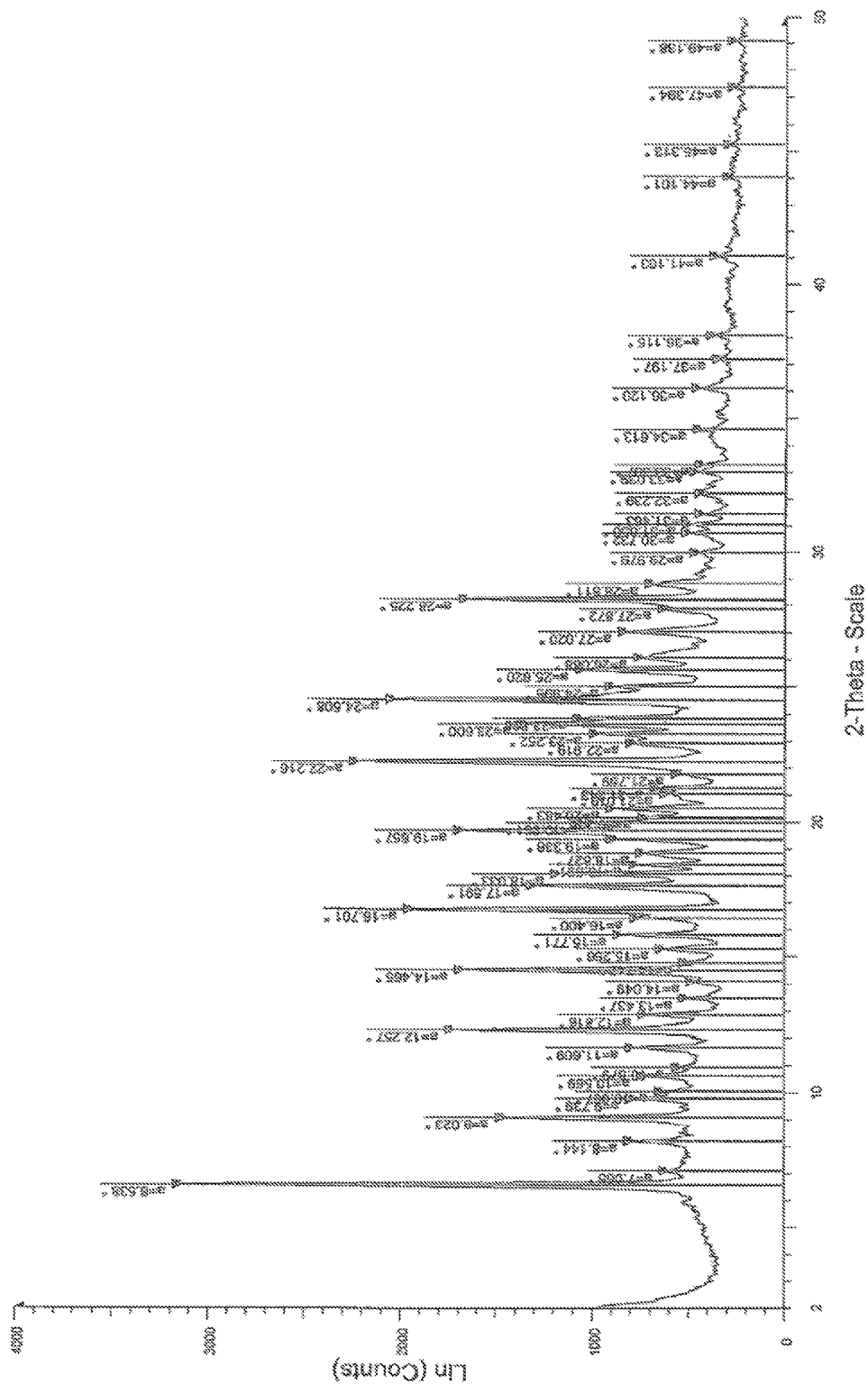
FIG. 1 is a graphical depiction of a characteristic XRPD pattern of ponatinib hydrochloride Form alpha according to an embodiment of the present disclosure.

In an embodiment, the present disclosure provides crystalline ponatinib hydrochloride propylene glycol solvate, designated as Form alpha, characterized by data selected from an XRPD pattern with peaks at about 6.5, 9.0, 12.25, 14.4, 16.70, 19.6, 22.2, 24.5, 28.2±0.2 degrees 2-theta; an XRPD pattern substantially as depicted in FIG. 1; and/or combinations thereof.

In another embodiment, the present disclosure provides a process for preparing ponatinib hydrochloride propylene glycol solvate designated Form alpha including the steps of:
 a. obtaining a solution of ponatinib hydrochloride and propylene glycol;
 b. maintaining the solution of step a) at a temperature of about 0° C. to about 150° C.; and
 c. isolating crystalline ponatinib hydrochloride propylene glycol solvate designated Form alpha from the solution.

Step a) involves obtaining a solution of ponatinib hydrochloride in propylene glycol solvent. Obtaining a solution according to step a) includes dissolving ponatinib hydrochloride in propylene glycol solvent or obtaining a solution of ponatinib hydrochloride in propylene glycol solvent as a final step in the preparation of the compound. Ponatinib hydrochloride may be obtained by a process known in the art.

The solution of step a) may be provided at any temperature ranging from about 0° C. to about reflux temperature of the solvent, preferably at about 50° C. to about 150° C., more preferably at about 100° C. to about 150° C., most preferably at about 100° C. to about 135° C.

The solution may optionally be treated with activated charcoal and then filtered to remove the carbon. The solution may optionally be filtered by passing through paper, glass fiber, or other membrane material, or a bed of a clarifying agent such as Celite®. Depending upon the equipment used, as well as the concentration and temperature of the solution, the filtration apparatus may need to be heated or cooled to avoid undesired crystallization.

Step b) involves maintaining the solution of step a) at a temperature of about 0° C. to about 150° C.

The solution of step a) is maintained at a temperature of about 0° C. to about 150° C. for sufficient time. Sufficient time as disclosed herein is the time required to ensure the formation of crystalline ponatinib hydrochloride. In an embodiment, the solution is maintained for a time period of about 30 minutes to about 50 hours.

In one embodiment step b) involves maintaining the solution of step a) at a temperature of about 20° C. to about 150° C. In an embodiment, the solution is maintained at a temperature of about 10° C. to about 40° C., more preferably at about 25° C. to about 35° C.

Optionally, seed crystals of Form alpha may be added to the solution of step a). The seed crystals of crystalline Form alpha may be obtained according to the process disclosed herein. The seeding may be performed at a temperature of about 0° C. to about 50° C. Preferably the seeding is performed at a temperature of at about 25° C. to about 35° C. In an embodiment, the solution of step a) is obtained after the seeding step.

Step c) involves isolating ponatinib hydrochloride Form alpha. The crystalline ponatinib hydrochloride Form alpha is isolated in accordance with any suitable method known to those having skill in the art, including but not limited to filtration by gravity or by suction/vacuum, distillation, centrifugation, or slow evaporation or the like. The appropriate isolation step should be employed in consideration of the solvent used. In an embodiment, ponatinib hydrochloride Form alpha may be isolated by filtration under vacuum and suction drying at a temperature of about 25° C. to about 35° C.

Drying the crystalline ponatinib hydrochloride Form alpha may be suitably carried out using any equipment such as a gravity oven, tray dryer, vacuum oven, Büchi® Rotavapor®, air tray dryer, fluidized bed dryer, spin flash dryer, flash dryer, and the like. In an embodiment, the drying may be carried out at atmospheric pressure or under reduced pressure. In an embodiment, the drying may be carried out at a temperature of about 120° C., at a temperature of about 115° C., at a temperature of about 110° C. or at a temperature of about 105° C. The drying may be carried out for any time period required for obtaining a desired quality, such as from about 15 minutes to several hours, or longer.

Figure 4:
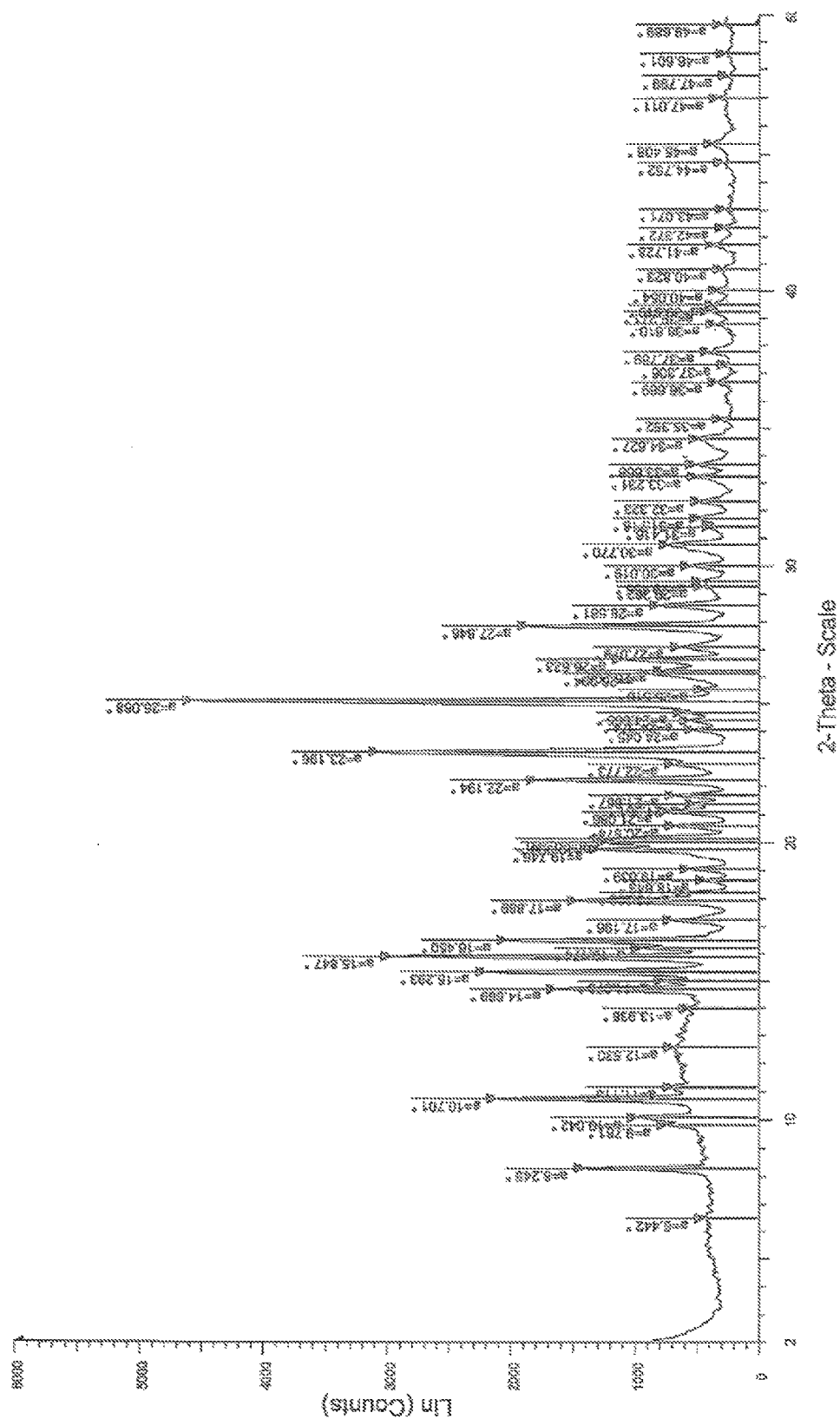
FIG. 4 is a graphical depiction of a characteristic XRPD pattern of ponatinib hydrochloride Form beta according to an embodiment of the present disclosure.

In an embodiment, the present application provides crystalline ponatinib hydrochloride benzyl alcohol solvate, designated as Form beta, characterized by data selected from an XRPD pattern with peaks at about 10.7, 15.2, 15.8, 16.4 23.1, 25.0, 27.8±0.2 degrees 2-theta; an XRPD pattern substantially as depicted in FIG. 4; and/or combinations thereof.

In another embodiment, the present application encompasses a process for preparing ponatinib hydrochloride Form beta comprising the steps of:
 a. obtaining a solution of benzyl alcohol and ponatinib hydrochloride;
 b. maintaining the solution of step a) at a temperature of about 0° C. to about 150° C.; and
 c. isolating ponatinib hydrochloride benzyl alcohol solvate designated Form beta from the solution.

Step a) involves obtaining a solution of ponatinib hydrochloride in benzyl alcohol solvent. Obtaining a solution according to step a) includes dissolving ponatinib hydrochloride in benzyl alcohol solvent or obtaining a solution of ponatinib hydrochloride in benzyl alcohol solvent as a final step in the preparation of the compound. Ponatinib hydrochloride may be obtained by process known in the art.

The solution of step a) may be provided at any temperature ranging from about 0° C. to about reflux temperature of the solvent, preferably at about 50° C. to about 150° C., more preferably at about 100° C. to about 150° C., most preferably at about 100° C. to about 135° C.

The solution may optionally be treated with activated charcoal and then filtered to remove the carbon. The solution may optionally be filtered by passing through paper, glass fiber, or other membrane material, or a bed of a clarifying agent such as Celite®. Depending upon the equipment used, as well as the concentration and temperature of the solution, the filtration apparatus may need to be heated or cooled to avoid undesired crystallization.

Step b) involves maintaining the solution of step a) at a temperature of about 0° C. to about 150° C.

The solution of step a) is maintained at a temperature of about of about 0° C. to about 150° C. for sufficient time. Sufficient time as disclosed herein is the time required to ensure the formation of crystalline ponatinib hydrochloride. In an embodiment, the solution is maintained for a time period of about 30 minutes to about 50 hours.

In one embodiment step b) involves maintaining the solution of step a) at a temperature of about 50° C. to about 150° C. In an embodiment, the solution is maintained at a temperature of about 10° C. to about 40° C., more preferably at about 25° C. to about 35° C.

Optionally, seed crystals of Form beta may be added to the solution of step a). The seed crystals of crystalline Form beta may be obtained according to the process disclosed herein. The seeding may be performed at a temperature of about 0° C. to about 50° C. Preferably the seeding is performed at a temperature of at about 25° C. to about 35° C. In an embodiment, the solution of step a) is obtained after the seeding step.

Step c) involves isolating ponatinib hydrochloride Form beta. The crystalline ponatinib hydrochloride Form beta is isolated in a manner in accordance with any suitable method known to those having skill in the art including but not limited to filtration by gravity or by suction/vacuum, distillation, centrifugation, or slow evaporation or the like. The appropriate isolation step should be employed in consideration of the solvent used. In an embodiment, ponatinib hydrochloride Form beta may be isolated by filtration under vacuum and suction drying at a temperature of about 25° C. to about 35° C.

Drying the crystalline ponatinib hydrochloride Form beta may be suitably carried out using any equipment such as a gravity oven, tray dryer, vacuum oven, Büchi® Rotavapor®, air tray dryer, fluidized bed dryer, spin flash dryer, flash dryer, and the like. In an embodiment, the drying may be carried out at atmospheric pressure or under reduced pressures. In an embodiment, the drying may be carried out at a temperature of about 120° C., at a temperature of about 115° C., at a temperature of about 110° C. or at a temperature of about 105° C. The drying may be carried out for any time period required for obtaining a desired quality, such as from about 15 minutes to several hours, or longer.

The crystalline forms of ponatinib hydrochloride designated as Form alpha and beta disclosed herein have advantageous properties selected from at least one of: chemical purity, stability, including but not limited to storage stability, stability to dehydration and stability to polymorphic conversion, flowability, solubility, morphology or crystal habit, low hygroscopicity and low content of residual solvents.

Certain specific aspects and embodiments of the present application will be explained in more detail with reference to the following examples and experiments, which are provided only for purposes of illustration and should not be construed as limiting the scope of the present application in any manner.

EXAMPLES AND EXPERIMENTS

Example-1 Preparation of Ponatinib Hydrochloride Form Alpha

Figure 2:
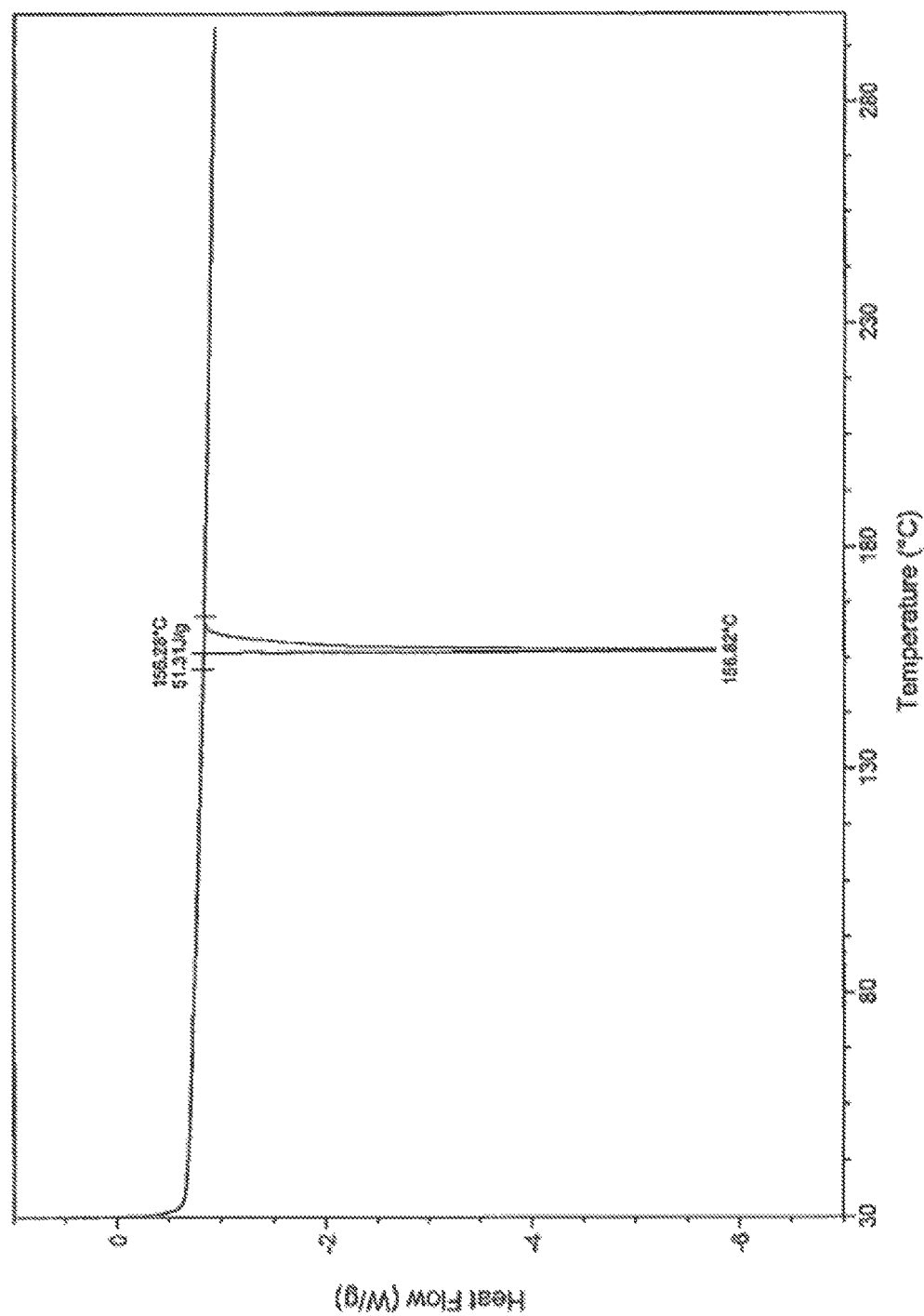
FIG. 2 is a graphical depiction of a DSC pattern of ponatinib hydrochloride Form alpha according to an embodiment of the present disclosure.

Ponatinib hydrochloride (10 g) and propylene glycol (30 ml) were charged into a round bottom flask and heated to 120-130° C. to obtain a clear solution. The solution was maintained at the same temperature for about 1.0 hour. The obtained clear solution was cooled to 20-30° C. and stirred for 30 minutes and further cooled to 0-5° C. and stirred for 12 hours. The obtained solid was stirred at 20-30° C. for 60 minutes and the solid was filtered and washed with chilled propylene glycol (5 ml) and dried under vacuum for 24 hours to obtain ponatinib hydrochloride propylene glycol solvate (Form alpha). An exemplary ponatinib hydrochloride Form alpha XRD pattern is shown in FIG. 1. An exemplary ponatinib hydrochloride Form alpha DSC is shown in FIG. 2.

Single Crystal XRD Method

Single crystal X-ray diffraction data on ponatinib hydrochloride were collected on 'Xcalibur, Eos, Gemini', CrysAlisPro, data reduction: Agilent Technologies Version 1.171.36.28, program(s) used to solve structure: 'SUPERFLIP, (J. Appl. Cryst. (2007) 40, 786790), program(s) used to refine structure: SHELX, (G. M. Sheldrick, Acta Cryst. (2008) A64, 112122), molecular graphics and software used to prepare material for publication: ORTEP3 (Farrugia, 1997) and O. V. Dolomanov, L. J. Bourhis, R. J. Gildea, J. A. K. Howard and H. Puschmann, OLEX2: a complete structure solution, refinement and analysis program (J. Appl. Cryst. (2009). 42, 339341).

Results

Figure 3:
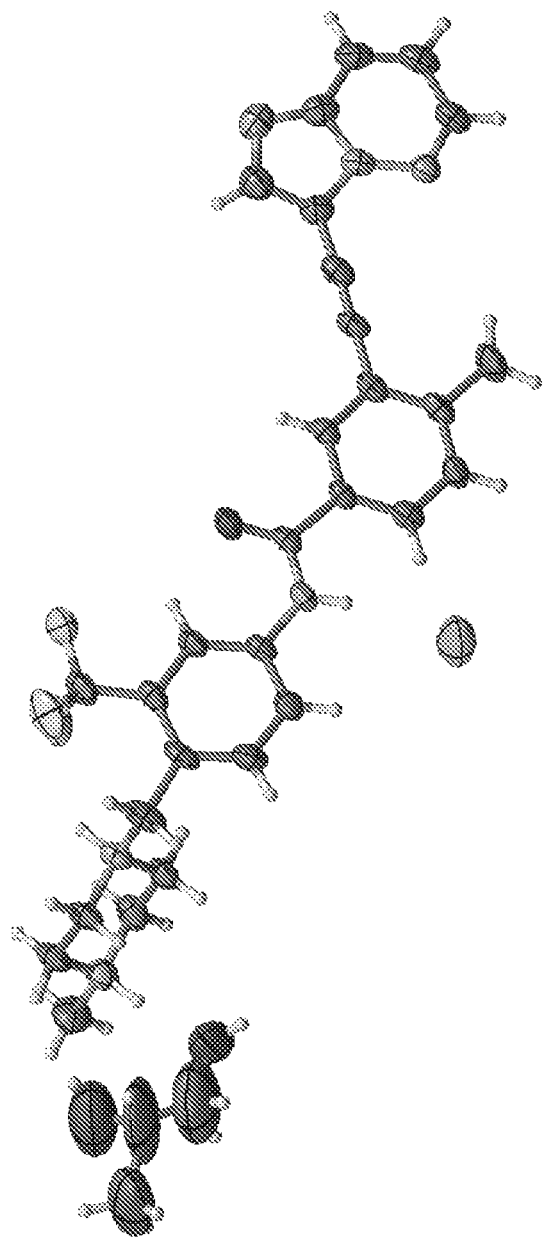
FIG. 3 is a diagrammatic representation of an X-ray crystal structure of ponatinib HCl Form alpha (thermal ellipsoid drawn at 50% probability) according to an embodiment of the present disclosure.

Ponatinib hydrochloride Form alpha crystallized into monoclinic crystal system with space group $P2_1/c$. Crystallographic data are shown in Table 1. FIG. 3 represents the ORTEP diagram of the molecules with thermal ellipsoids drawn at 50% probability. The crystal structure of Form alpha confirms ponatinib HCl propylene glycol solvate. The solvent ratio of propylene glycol in Form alpha was found to be one mole (monosolvate).

TABLE 1

| Crystal data and structure refinement for Ponatinib HCl Form alpha | |
|---|---|
| Empirical formula | $C_{29}H_{26}F_3N_6O_1Cl_1 \cdot C_3H_8O_2$ |
| Formula weight | 645.12 |
| Temperature/K | 293(2) |
| Crystal system | Monoclinic |
| Space group | $P2_1/c$ |
| a/Å | 9.6868(10) |
| b/Å | 26.732(3) |
| c/Å | 14.4937(12) |
| α/° | 90 |
| β/° | 98.068(9) |
| γ/° | 90 |
| Volume/Å3 | 3716.0(7) |
| Z | 4 |
| ρcalcg/cm3 | 0.683 |
| μ/mm-1 | 0.083 |
| Radiation | Mo (λ = 0.71073) |
| Index ranges | $-13 \leq h \leq 12, -36 \leq k \leq 34, -11 \leq l \leq 19$ |
| Reflections collected | 22073 |
| Independent reflections | 8591 [$R_{int}$ = 0.0696, $R_{sigma}$ = 0.1069] |
| Goodness-of-fit on F2 | 1.039 |
| Final R indexes [I >= 2σ (I)] | R1 = 0.1203, wR2 = 0.3401 |

Example-2 Preparation of Ponatinib Hydrochloride Form Beta

Figure 5:
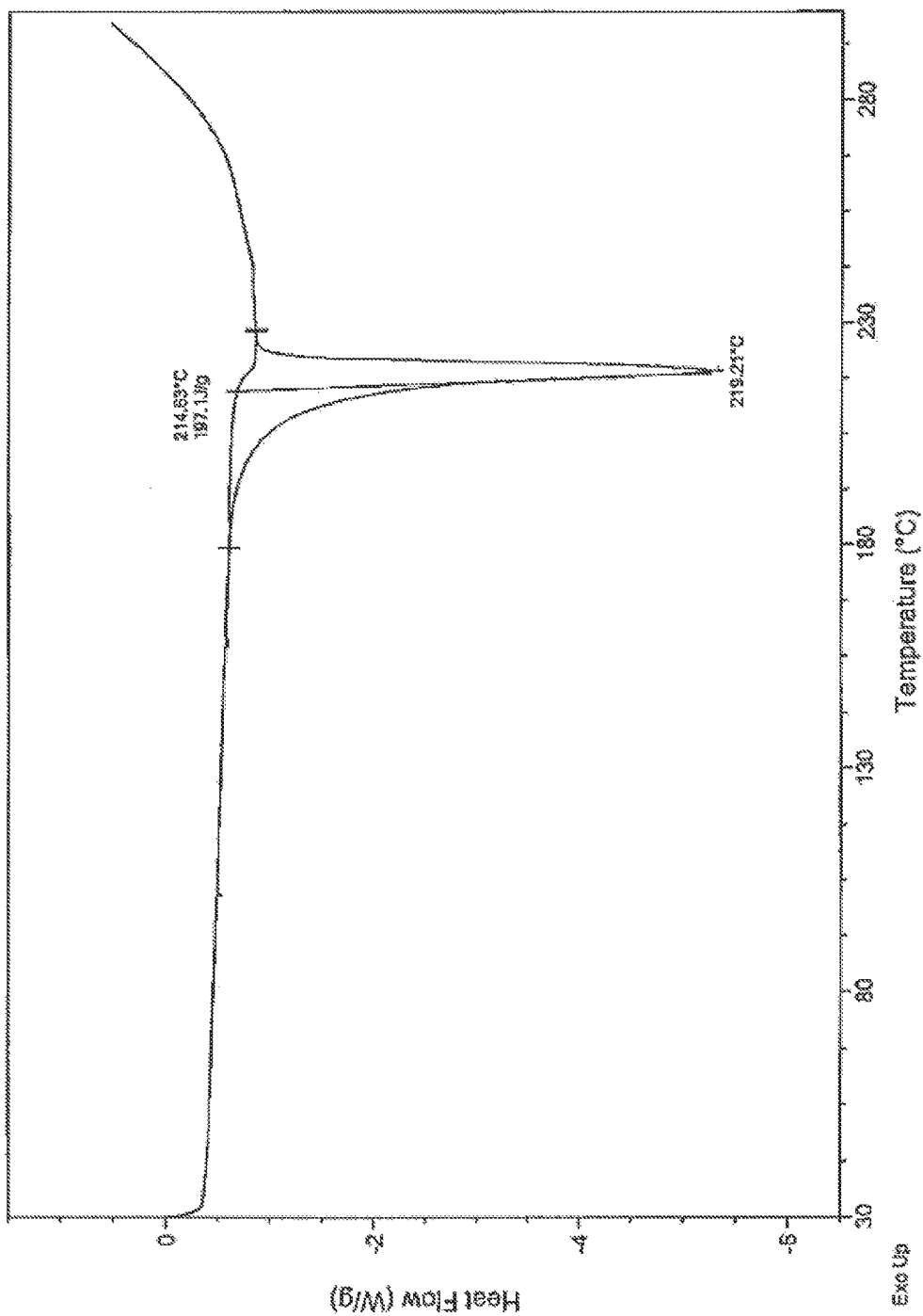
FIG. 5 is a graphical depiction of a DSC pattern of ponatinib hydrochloride Form beta according to an embodiment of the present disclosure.

Ponatinib hydrochloride (10 g) and benzyl alcohol (20 ml) were charged into a round bottom flask and heated to 150° C. to obtain a clear solution. The solution was maintained at the same temperature for about 1.0 hour. The obtained clear solution was cooled to 20-30° C. and stirred for 2 hrs. The obtained solid was filtered and washed with benzyl alcohol 5 ml, suction dried, dried in a vacuum tray for about 24 hours to obtain ponatinib hydrochloride Form beta. An exemplary ponatinib hydrochloride Form beta XRD pattern is shown in FIG. 4. An exemplary ponatinib hydrochloride Form beta DSC is shown in FIG. 5.

Single Crystal XRD Method

Single crystal X-ray diffraction data on ponatinib hydrochloride were collected on 'Xcalibur, Eos, Gemini', Crys- AlisPro, data reduction: Agilent Technologies Version 1.171.36.28, program(s) used to solve structure: 'SUPER-FLIP, (J. Appl. Cryst. (2007) 40, 786790), program(s) used to refine structure: SHELX, (G. M. Sheldrick, Acta Cryst. (2008) A64, 112122), molecular graphics and software used to prepare material for publication: ORTEP3 (Farrugia, 1997) and O. V. Dolomanov, L. J. Bourhis, R. J. Gildea, J. A. K. Howard and H. Puschmann, OLEX2: a complete structure solution, refinement and analysis program (J. Appl. Cryst. (2009). 42, 339341).

Results

Figure 7:
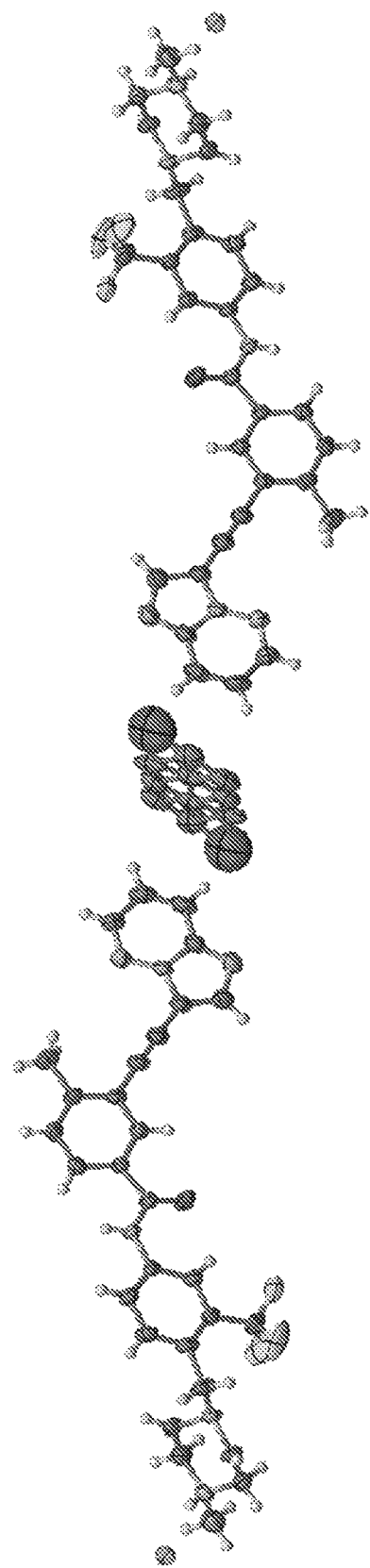
FIG. 7 is a diagrammatic representation of an X-ray crystal structure of ponatinib HCl Form beta showing structural disorder presented by the presence of benzyl alcohol according to an embodiment of the present disclosure.

Ponatinib hydrochloride Form beta crystallized into triclinic crystal system with space group P-1. Crystallographic data are shown in Table 2. FIGS. 6 and 6A represent the ORTEP diagram of the molecules with thermal ellipsoids drawn at 50% probability. FIG. 7 shows the disorder due to the presence of benzyl alcohol in Form beta. The crystal structure of Form beta confirms ponatinib HCl benzyl alcohol hemisolvate. The solvent ratio of benzyl alcohol in Form beta was found to be hemi mole (0.5 mole). An XRPD comparison of simulated and experimental further confirms the phase purity of Form beta.

TABLE 2

Crystal data and structure refinement for Ponatinib HCl Form beta

| | |
|---|---|
| Empirical formula | $2(C_{29}H_{26}F_3N_6O_1Cl_1) \cdot C_7H_8O_1$ |
| Formula weight | 1173.26 |
| Temperature/K | 293(2) |
| Crystal system | triclinic |
| Space group | P-1 |
| a/Å | 10.0656(6) |
| b/Å | 11.9216(8) |
| c/Å | 14.1811(9) |
| α/° | 83.719(5) |
| β/° | 82.662(5) |
| γ/° | 65.892(6) |
| Volume/Å3 | 1537.47(16) |
| Z | 2 |
| pcalcg/cm3 | 1.512 |
| μ/mm-1 | 0.183 |
| Radiation | Mo (λ = 0.71073) |
| Index ranges | $-13 \leq h \leq 12, -15 \leq k \leq 16,$ $-19 \leq l \leq 18$ |
| Reflections collected | 12330 |
| Independent reflections | 8132 [$R_{int}$ = 0.0206, $R_{sigma}$ = 0.0381] |
| Goodness-of-fit on F2 | 1.038 |
| Final R indexes [I >= 2σ (I)] | R1 = 0.0706, wR2 = 0.1955 |

Although the compounds, schemes and methods of the present disclosure have been described with reference to exemplary embodiments thereof, the present disclosure is not limited thereby. Indeed, the exemplary embodiments are implementations of the disclosed methods are provided for illustrative and non-limitative purposes. Changes, modifications, enhancements and/or refinements to the disclosed methods may be made without departing from the spirit or scope of the present disclosure. Accordingly, such changes, modifications, enhancements and/or refinements are encompassed within the scope of the present invention. All publications, patent applications, patents, figures and other references mentioned herein are expressly incorporated by reference in their entirety.

What is claimed is:

1. Crystalline ponatinib hydrochloride propylene glycol monosolvate Form alpha, characterized by data selected from an x-ray powder diffraction pattern (XPRD) with peaks at about 6.5, 9.0, 12.25, 14.4, 16.70, 19.6, 22.2, 24.5, 28.2±0.2 degrees 2-theta.

2. Crystalline ponatinib hydrochloride propylene glycol monosolvate Form alpha according to claim 1 characterized by an XPRD pattern substantially as depicted in FIG. 1.

3. A process for preparing ponatinib hydrochloride propylene glycol monosolvate Form alpha according to claim 1 comprising the steps of:
   a) obtaining a solution of ponatinib hydrochloride and propylene glycol;
   b) maintaining the solution of step a) at a temperature of about 0° C. to about 150° C.; and
   c) isolating crystalline ponatinib hydrochloride propylene glycol monosolvate Form alpha from the solution of step b).

4. The process according to claim 3 wherein step b) comprises maintaining the solution of step a) at a temperature of about 20° C. to about 150° C.

5. The process according to claim 3 wherein step b) comprises maintaining the solution of step a) at a temperature of about 25° C. to about 35° C.

6. The process according to claim 3 further comprising adding seed crystals of Form alpha to the solution of step a).

7. Crystalline ponatinib hydrochloride benzyl alcohol hemisolvate Form beta, characterized by data selected from an XRPD pattern with peaks at about 10.7, 15.2, 15.8, 16.4, 23.1, 25.0, 27.8±0.2 degrees 2-theta.

8. Crystalline ponatinib hydrochloride benzyl alcohol hemisolvate Form beta according to claim 7, characterized by an XRPD pattern substantially as depicted in FIG. 4.

9. A process for preparing ponatinib hydrochloride benzyl alcohol hemisolvate Form beta according to claim 7 comprising the steps of:
   a) obtaining a solution of ponatinib hydrochloride and benzyl alcohol;
   b) maintaining the solution of step a) at a temperature of about 0° C. to about 150° C.; and
   c) isolating ponatinib hydrochloride benzyl alcohol hemisolvate Form beta from the solution of step b).

10. The process of claim 9 wherein step b) comprises maintaining the solution of step a) at a temperature of about 50° C. to about 150° C.

11. The process of claim 9 wherein step b) comprises maintaining the solution of step a) at a temperature of about 25° C. to about 35° C.

12. The process according to claim 9 further comprising adding seed crystals of Form beta to the solution of step a).

* * * * *